United States Patent [19]

Wong et al.

[11] Patent Number: 5,731,427
[45] Date of Patent: Mar. 24, 1998

[54] NUCLEIC ACIDS ENCODING A GAP-ASSOCIATED PROTEIN

[75] Inventors: Gail L. Wong, La Jolla; Francis P. McCormick, Berkeley, both of Calif.

[73] Assignee: Chiron Corporation, Emeryville, Calif.

[21] Appl. No.: 438,883

[22] Filed: May 10, 1995

Related U.S. Application Data

[62] Division of Ser. No. 702,771, May 17, 1991, Pat. No. 5,610,276.

[51] Int. Cl.⁶ .................................................. C07H 21/04
[52] U.S. Cl. ........................... 536/23.5; 530/358; 435/6
[58] Field of Search .................. 435/6, 7.1; 536/24.31, 536/23.5; 530/358

[56] References Cited

PUBLICATIONS

Ellis et al., Nature (Jan. 25, 1990) 343:377–381.
Boguski et al., Nature (Dec. 16, 1993) 366(6456):643–654.

*Primary Examiner*—Scott W. Houtteman
*Attorney, Agent, or Firm*—Donald J. Pochopien; Jane E. R. Potter; Robert P. Blackburn

[57] ABSTRACT

The subject invention provides for nucleotide sequences encoding polypeptide p62 and derivatives thereof. Another aspect of the subject invention also provides for methods of purifying p62 and derivatives thereof from cells naturally producing p62 and from cells genetically modified so as to produce p62. The subject invention also provides for methods of assaying tyrosine kinase activity by means of measuring the phosphorylation of p62 and p62 derivatives. Measurement of p62/p62 derivative phosphorylation may be used to determine whether or not a call is cancerous.

14 Claims, 6 Drawing Sheets

FIG. 1A

```
     421  GCAGGAAGAGACTGGTGCAAAGATCTCTGTATTGGGAAAGGGCTCAATGAGAGACAAAGC  480
←GW79     CGTCCTTCTCTGACCACGTTTCTAGAGACATAACCCTTTCCCGAGTTACTCTCTGTTTCG a          A  G  R  D  W  C  K  D  L  C  I  G  K  G  L  N  E  R  Q  S   -
b           Q  E  E  T  G  A  K  I  S  V  L  G  K  G  S  M  R  D  K  A  -
c            R  K  R  L  V  Q  R  S  L  Y  W  E  R  A  Q  *  E  T  K  P -

481  CAAGGAGGAAGAGCTGCGCAAAGGTGGAGACCCCAAATATGCCCACTTGAATATGGATCT  540
          GTTCCTCCTTCTCGACGCGTTTCCACCTCTGGGGTTTATACGGGTGAACTTATACCTAGA a          Q  G  G  R  A  A  Q  R  W  R  P  Q  I  C  P  L  E  Y  G  S   -
b           K  E  E  E  L  R  K  G  G  D  P  K  Y  A  H  L  N  M  D  L  -
c            R  R  K  S  C  A  K  V  E  T  P  N  M  P  T  *  I  W  I  C -

541  GCATGTCTTCATTGAAGTCTTTGGACCCCCATGTGAGGCTTATGCTCTTATGGCCCATGC  600
          CGTACAGAAGTAACTTCAGAAACCTGGGGGTACACTCCGAATACGAGAATACCGGGTACG a          A  C  L  H  *  S  L  W  T  P  M  *  G  L  C  S  Y  G  P  C   -
b           H  V  F  I  E  V  F  G  P  P  C  E  A  Y  A  L  M  A  H  A  -
c            M  S  S  L  K  S  L  D  P  H  V  R  L  M  L  L  W  P  M  P -

601  CATGGAGGAAGTCAAGAAATTTCTAGTACCGGATATGATGGATGATATCTGTCAGGAGCA  660
          GTACCTCCTTCAGTTCTTTAAAGATCATGGCCTATACTACCTACTATAGACAGTCCTCGT a          H  G  G  S  Q  E  I  S  S  T  G  Y  D  G  *  Y  L  S  G  A   -
b           M  E  E  V  K  K  F  L  V  P  D  M  M  D  D  I  C  Q  E  Q  -
c            W  R  K  S  R  N  F  *  Y  R  I  *  W  M  I  S  V  R  S  N -

661  ATTTCTAGAGCTGTCCTACTTGAATGGAGTACCTGAACCCTCTCGTGGACGTGGGGTGCC  720
          TAAAGATCTCGACAGGATGAACTTACCTCATGGACTTGGGAGAGCACCTGCACCCCACGG a          I  S  R  A  V  L  L  E  W  S  T  *  T  L  S  W  T  W  G  A   -
b           F  L  E  L  S  Y  L  N  G  V  P  E  P  S  R  G  R  G  V  P  -
c            F  *  S  C  P  T  *  M  E  Y  L  N  P  L  V  D  V  G  C  Q -

721  AGTGAGAGGCCGGGGAGCTGCACCTCCTCCACCACCTGTTCCCAGGGGCCGTGGTGTTGG  780
          TCACTCTCCGGCCCCTCGACGTGGAGGAGGTGGTGGACAAGGGTCCCCGGCACCACAACC a          S  E  R  P  G  S  C  T  S  S  T  T  C  S  Q  G  P  W  C  W   -
b           V  R  G  R  G  A  A  P  P  P  P  P  V  P  R  G  R  G  V  G  -
c            *  E  A  G  E  L  H  L  L  H  H  L  F  P  G  A  V  V  L  D -

781  ACCACCTCGGGGGGCTTTGGTACGTGGTACACCAGTAAGGGGAGCCATCACCAGAGGTGC  840
          TGGTGGAGCCCCCCGAAACCATGCACCATGTGGTCATTCCCCTCGGTAGTGGTCTCCACG a          T  T  S  G  G  F  G  T  W  Y  T  S  K  G  S  H  H  Q  R  C   -
b           P  P  R  G  A  L  V  R  G  T  P  V  R  G  A  I  T  R  G  A  -
c            H  L  G  G  L  W  Y  V  V  H  Q  *  G  E  P  S  P  E  V  P -

841  CACTGTGACTCGAGGCGTGCCACCCCCACCTACTGTGAGGGGTGCTCCAGCACCAAGAGC  900
          GTGACACTGAGCTCCGCACGGTGGGGGTGGATGACACTCCCCACGAGGTCGTGGTTCTCG
```

ACGGACAGCGGGCATCCAGAGGATACCTTTGCCTCCACCTCCTGCACCAGAAACATATGA
901    ----------+----------+----------+----------+----------+----------+    960
       TGCCTGTCGCCCGTAGGTCTCCTATGGAAACGGAGGTGGAGGACGTGGTCTTTGTATACT a       T  D  S  G  H  P  E  D  T  F  A  S  T  S  C  T  R  N  I  *    -
b      R  T  A  G  I  Q  R  I  P  L  P  P  P  P  A  P  E  T  Y  E    -
c       G  Q  R  A  S  R  G  Y  L  C  L  H  L  L  H  Q  K  H  M  K    -

AGAATATGGATATGATGATACATACGCAGAACAAAGTTACGAAGGCTACGAAGGCTATTA
961    ----------+----------+----------+----------+----------+----------+    1020
       TCTTATACCTATACTACTATGTATGCGTCTTGTTTCAATGCTTCCGATGCTTCCGATAAT a       R  I  W  I  *  *  Y  I  R  R  T  K  L  R  R  L  R  R  L  L    -
b      E  Y  G  Y  D  D  T  Y  A  E  Q  S  Y  E  G  Y  E  G  Y  Y    -
c       N  M  D  M  M  I  H  T  Q  N  K  V  T  K  A  T  K  A  I  T    -

CAGCCAGAGTCAAGGGGACTCAGAATATTATGACTATGGACATGGGGAGGTTCAAGATTC
1021   ----------+----------+----------+----------+----------+----------+    1080
       GTCGGTCTCAGTTCCCCTGAGTCTTATAATACTGATACCTGTACCCCTCCAAGTTCTAAG a       Q  P  E  S  R  G  L  R  I  L  *  L  W  T  W  G  G  S  R  F    -
b      S  Q  S  Q  G  D  S  E  Y  Y  Y  D  Y  G  H  G  E  V  Q  D  S  -
c       A  R  V  K  G  T  Q  N  I  M  T  M  D  M  G  R  F  K  I  L    -

TTATGAAGCTTATGGCCAGGACGACTGGAATGGGACCAGGCCGTCGCTGAAGGCCCCTCC
1081   ----------+----------+----------+----------+----------+----------+    1140
       AATACTTCGAATACCGGTCCTGCTGACCTTACCCTGGTCCGGCAGCGACTTCCGGGGAGG a       L  *  S  L  W  P  G  R  L  E  W  D  Q  A  V  A  E  G  P  S    -
b      Y  E  A  Y  G  Q  D  D  W  N  G  T  R  P  S  L  K  A  P  P    -
c       M  K  L  M  A  R  T  T  G  M  G  P  G  R  R  *  R  P  L  L    -

TGCTAGGCCAGTGAAGGGAGCATACAGAGAGCACCCATATGGACGT TAT AAAAACAAAC
1141   ----------+----------+----------+----------+----------+----------+    1200
       ACGATCCGGTCACTTCCCTCGTATGTCTCTCGTGGGTATACCTGCAATAATTTTTGTTTG a       C  *  A  S  E  G  S  I  Q  R  A  P  I  W  T  L  L  K  T  N    -
b      A  R  P  V  *  K  G  A  Y  R  E  H  P  Y  G  R  Y  *  K  Q  T  -
c       L  G  Q  *  R  E  H  T  E  S  T  H  M  D  V  I  K  N  K  H    -

ATGAGGGGAAAATATCAGTTATGAGCAAAGTTGTTACTGATTTCTTGTATCTCCCAGGAT
1201   ----------+----------+----------+----------+----------+----------+    1260
       TACTCCCCTTTTATAGTCAATACTCGTTTCAACAATGACTAAAGAACATAGAGGGTCCTA a       M  R  G  K  Y  Q  L  *  A  K  L  L  L  I  S  C  I  S  Q  D    -
b      *  G  E  N  I  S  Y  E  Q  S  C  Y  *  F  L  V  S  P  R  I    -
c       E  G  K  I  S  V  M  S  K  V  V  T  D  F  L  Y  L  P  G  F    -

TCCTGTTGCTTTACCCACAACAGACAAGTAATTGTCTAAGTGTTTTTCTTCGTGGTCCCC
1261   ----------+----------+----------+----------+----------+----------+    1320
       AGGACAACGAAATGGGTGTTGTCTGTTCATTAACAGATTCACAAAAAGAAGCACCAGGGG a       S  C  C  F  T  H  N  R  Q  V  I  V  *  V  F  F  F  V  V  P    -
b      P  V  A  L  P  T  T  D  K  *  L  S  K  C  F  S  S  W  S  P    -
c       L  L  L  Y  P  Q  Q  T  S  N  C  L  S  V  F  L  R  G  P  L    -
```

FIG. 1C

```
        TTCTTCTCCCCACCTTATTCCATTCTTAACTCTGCATTCTGGCTTCTGTATGTAGTATTT
1321    ----------+----------+----------+----------+----------+----------+   1380
        AAGAAGAGGGGTGGAATAAGGTAAGAATTGAGACGTAAGACCGAAGACATACATCATAAA a        F  F  S  P  P  Y  S  I  L  N  S  A  F  W  L  L  Y  V  V  F   -
b         S  S  P  H  L  I  P  F  L  T  L  H  S  G  F  C  M  *  Y  F  -
c          L  L  P  T  L  F  H  S  *  L  C  I  L  A  S  V  C  S  I  L -

TAAAATGAGTTAAAATAGATTTAGGAATATTGAATTAATTTTTTAAGTGTGTAGATGCTT
1381    ----------+----------+----------+----------+----------+----------+   1440
        ATTTTACTCAATTTTATCTAAATCCTTATAACTTAATTAAAAAATTCACACATCTACGAA a        *  N  E  L  K  *  I  *  E  Y  *  I  N  F  L  S  V  *  M  L   -
b         K  M  S  *  N  R  F  R  N  I  E  L  I  F  F  *  V  C  R  C  F  -
c          K  *  V  K  I  D  L  G  I  L  N  *  F  F  K  C  V  D  A  F -

TTTTCTTTGTTGTTTAAATATAAACAGAAGTGTACCTTTTATAAT
1441    ----------+----------+----------+----------+-----   1485
        AAAAGAAACAACAAATTTATATTTGTCTTCACATGGAAAATATTA a        F  S  L  L  F  K  Y  K  Q  K  C  T  F  Y  N  ?   -
b         F  L  C  C  L  N  I  N  R  S  V  P  F  I  ?    -
c          F  F  V  V  *  I  *  T  E  V  Y  L  L  *  ?   -
```

FIG. 1D

```
             30         40         50         60         70
Pg1101   CACTATAGGGCGAATTCGGGCGACCCCGCTGCTGCCCCCCTCG-GCCACAGCCTCGGT--
              ||||||   |  ||  ||   |||||  ||
Shrgrp   TGTATTTGATAATTAAGGTATAAAAAAATGGCTGCCAAACCCGAGCAAGAGCCTGTGTAT
             20         30         40         50         60         70

80         90         100        110        120        130
Pg1101   ---CAAGATGGAGCCAGAGAACAAGTACCTGCCCG--AACTCATGGC-CGAGAAGGACTC
            |  ||||    |||    |||  |||  ||||   ||  |   |    ||  ||||| |
Shrgrp   GTCCGAGATTTGGTGAAAGATTATGATGATGCTCGTCAAATGCTAACTCAAGCAGGAGTA
             80         90         100        110        120        130

140        150        160        170        180        190
Pg1101   GCTCGACCCGTCCTTCACTCACGCCATGCAG--CTGCTGACGGCAGAAATTGAGAAGATT
          | |  | ||  |||    ||    ||||||    |  |    ||||  |||| ||   |
Shrgrp   TCTGAAGCAGTACTTGGAACAATAGATGCAGAAATCAAGCACATAAAAACTGGAAGTCGG
             140        150        160        170        180        190

200        210        220        230        240
Pg1101   CAGAAAGGAGACTCAAAAAAGGAT-GATGAGGAGAATTACTTGGATTTATTTTCTCATAA
          |||||    ||   |||    || ||| |||   ||| | |||| |||    |||  |
Shrgrp   CCGAAAACCGTGCCAAATACAGATGGATCTG--GATTTA--TGGATCTTTACAATGACAC
             200        210        220        230        240        250

250        260        270        280        290        300
Pg1101   GAACATGAAACTGAAAGAGCGAGTGCTG-ATACCTGTCAAGCAGTATCCCAAGTTCAATT
          ||  |||||        ||  || || || |   | ||| | | | ||||||| |||  |
Shrgrp   CAAAGTTAAACTTGTTTCAAGA-TGTTGCTTGCCTGTTGATCAATTCCCCAAGTACAACT
             260        270        280        290        300        310

310        320        330        340        350        360
Pg1101   TTGTGGGGAAGATTCTTGGACCACAAGGGAATACAATCAAAAGACTGCAGGAAGAGACTG
          |  || ||  ||||||||||| |  |||  |  |||   |  ||| || || || ||
Shrgrp   TCCTTGGTAAACTTCTTGGACCTGGTGGAAGCACCATGAAACAACTTCAAGATGAAACGA
             320        330        340        350        360        370

370        380        390        400        410        420
Pg1101   GTGCAAAGATCTCTGTATTGGGAAAGGGCTCAATGAGAGACAAAGCCAAGGAGGAAGAGC
          |||||  || |  |    ||||  |||||||||||||||||  |    ||||| |||||  |||||
Shrgrp   TGACTAAGATTTCAATCCTTGGAAGAGGCTCAATGAGAGATAGGAACAAGGAAGAAGAAT
             380        390        400        410        420        430

430        440        450        460        470        480
Pg1101   TGCGCAAAGGTGGAGACCCCAAATATGCCCACTTGAATATGGATCTGCATGTCTTCATTG
          || | ||  ||||||  |||||||||||||||||  |  ||| ||  ||  | | | |
Shrgrp   TGAGGAATTCAGGAGACGTCAAATATGCCCACTTGAACGAGCAGCTCCACAT-TGAGATC
             440        450        460        470        480

490        500        510        520        530        540
Pg1101   AAGTCT-TTGGACCCCCATGTGAGGCTTATGCTCTTATGGCCCATGCCATGGAGGAAGTC
          ||| ||  |||   ||||| ||||||| |||||  |||||| |||||| |||   |||  ||
Shrgrp   ATTTCTATTGCTAGTCCTGCTGAGGCTCATGCCCGTATGGCCTATGCTCTCACTGAAATC
             490        500        510        520        530        540

550        560        570        580        590        600
Pg1101   AAGAAATTTCT-AGTACCGGATATGATGGATGATATCTGTCAGGAGCAATTTCTAGAGCT
          |||||  |  | |||| | ||||||||||||| | ||   ||   ||   |||| ||
Shrgrp   AAGAAGTATATCACCCCAGAAGAGGATCCAAACTACATGATGATGGCCGGTCATGGCGCT
             550        560        570        580        590        600

610        620
Pg1101   -GTCCTACTTGATGAGTAC
          |||||| ||||||| |
Shrgrp   GGTCCAA--TGATGGGCATGGGAGGTATGATGGGAGGTCCAGGGCCAATGGGACCACAAG
             610        620        630        640        650        660
```

FIG. 2

```
              10        20        30        40        50
Pg1101  IVIRLTIGRIRATPLLPPSATASVKMEPENKYLPELMAEKDSLDPSFTHA------MQLL
              ::| |:|   |:::|:  : |:    :|:|                :   :
A29379                      MAAKPEQEPVYVRDLVKDYDDARQMLTQAGVSEAVLGTI
                                   10        20        30

60        70        80        90       100       110
Pg1101  TAEIEKIQKGDSKK----DDEENYLDLFSHKNMKLKERVLIPVKQYPKFNFVGKILGPQG
        ;|||::|::|::  |    :|::::||:::;:||  :|   :||:|:||:||:|||  |
A29379  DAEIKHIKTGSRPKTVPNTDGSGFMDLYNDTKVKLVSRCCLPVDQFPKYNFLGKLLGPGG
         40        50        60        70        80        90

120       130       140       150       160       170
Pg1101  NTIKRLQEETGAKISVLGKGSMRDKAKEEELRKGGDPKYAHLNMDLHVFIEVFGPPCEAY
        :|:|:||:||  :|||:||:|||||:||||||::||  ||||||  ||:||: |   ||:
A29379  STMKQLQDETMTKISILGRGSMRDRNKEEELRNSGDVKYAHLNEQLHIEIISIASPAEAH
        100       110       120       130       140       150

180       190       200
Pg1101  ALMAHAMEEVKKFLVPDMMDDICQEQFLELSYLMS
        | ||:|:::|:||::::|:
A29379  ARMAYALTEIKKYITPEEDPNYMMMAGHGAGPMMGMGGMMGGPGPMGPQGRGRGRGRGGF
        160       170       180       190       200       210
```

FIG. 3

NUCLEIC ACIDS ENCODING A GAP-ASSOCIATED PROTEIN

This application is a divisional of application Ser. No. 07/702,771, filed May 17, 1991 now U.S. Pat. No. 5,610,276.

FIELD OF THE INVENTION

The present invention relates to the field of molecular biology in general, and the field of oncogene binding proteins in particular.

BACKGROUND OF THE INVENTION

Most phosphorylated cellular proteins are phosphorylated on threonine and serine residues; however, an important class of proteins is phosphorylated on tyrosine residues. Tyrosine kinase activity has been found in a number of membrane bound ligand receptors, such as the epidermal growth factor (EGF) receptor and the insulin receptor. Furthermore, a number of oncogenes encode proteins that have tyrosine kinase activity, these oncogenes include v-erb, v-fps, v-abl, and v-src. The phosphorylation of specific proteins by tyrosine kinases is believed to have important physiological consequences for the cell.

Identified substrates for tyrosine kinases include the GAP protein. Guanosine triphosphatase (GTPase) activator protein, referred to as GAP, stimulates the weak intrinsic GTPase activity of normal ras. GAP acts on normal ras p21 and converts it to a ras p21.GDP complex. In contrast, oncogenic forms of ras p21 are not sensitive to GAP, and persist as ras p21.GTP complexes. It is believed that GAP may attenuate signaling by normal ras p21.GTP. Some studies suggest that GAP may itself be the effector through which ras p21.GTP transmits a mitogenic signal to the cell. Mutagenesis of the GAP interaction domain on oncogenic forms of ras p21 blocks signaling. McCormick, F., 1989, Cell, 56: 5; Adari. H., et al., 1988 Nature, 352: 548. Injection of a truncated form of ras p21, that has an increased affinity for GAP into Xenopus oocyte blocked some effects of oncogenically activated ras, and excess GAP overcome this inhibition. Gibbs, J. B., et al., 1989, Proc. Natl. Acad. Sci. USA, 86: 6630. Krevi, a protein that blocks the transforming effects of oncogenic ras mutants on cells is very similar to ras in the GAP-binding domain and may act by competing with ras for binding to GAP. Kitayama, H., et al. 1989, Cell, 56: 77.

Experiments have shown that GAP is spatially associated with other proteins that are phosphorylated on tyrosine in cells that have been transformed by cytoplasmic and receptor-like tyrosine kinases. Immunoprecipitation of proteins in transformed mouse fibroblasts with GAP specific antiserum coprecipitates several proteins. When GAP immunoprecipitates are separated by SDS_PAGE, western blotted to nitrocelluiose, and subsequently probed with anti-phosphotyrosine specific antibodies, bands with relative molecular weight of 62,000 and 190,000 daltons, p62 and p190, respectively) are revealed; Ellis et al., Nature 343:377–381 (1990). GAP, p62 and p190, have been shown to be tyrosine phosphorylated in cells transformed by v-src, v-abl, and h-ras, as well as being tyrosine phosphorylated in response to stimulation of cells by EGF (Ellis, ibid.). The p62 protein has also been shown to specifically associate with the SH2 domain of GAP by means of experiments in which bacterially produced SH2 domains of GAP were reconstituted in vitro with p62. Moran et al, Function and Evolution of Ras Proteins, Cold Spring Harbor, N.Y. (1990). Furthermore, it has also been found that activated platelet derived growth factor receptor also binds to GAP, indicating that GAP may be involved in mediating PDGF's biological actions, Kazlanskas, Science, 247:1578 (1990).

SUMMARY OF THE INVENTION

The subject invention provides for nucleotide sequences encoding polypeptide p62 and derivatives thereof. Another aspect of the subject invention is to provide methods of purifying p62 and derivatives thereof from cells naturally producing p62 and from cells genetically modified so as to produce p62.

The subject invention also provides for methods of assaying tyrosine kinase activity by means of measuring the phosphorylation of p62. Additionally, the percentage of phosphorated p62 relative to total p62 in a cell may be measured. The phosphorylation of p62 may be used to determine whether or not a cell is transformed or has the potential to become cancerous, and to measure the receptor binding of various growth factors. Another aspect of the invention is to provide for antibodies that may be used in the p62 assays.

BRIEF DESCRIPTION OF THE DRAWINGS

FIGS. 1a to 1d depict the DNA and amino acid sequence of SEQ ID NO: 2.

FIG. 2 depicts a comparison of homologous nucleotide sequences of p62 coding sequence and the coding sequence of the Artemia salina glycine-rich protein GRP33.

FIG. 3 depicts a comparison of homologous amino acid sequences of the p62 protein and the A. salina glycine-rich protein GRP33.

DESCRIPTION OF THE SPECIFIC EMBODIMENTS

The present invention provides for purified p62 and p62 derivatives that possess the biological and/or immunological properties of p62. The present invention also provides for purified nucleic acid sequences encoding p62 and various derivatives of p62, and immunological reagents capable of specifically binding p62. Also provided for are various assays, including assays for the measurement of tyrosine kinase activity, the measurement of the extent of phosphorylation of p62 in a cell, and assays for the detection of p62.

The term p62, as used herein, is defined to include proteins that have p62 biological activity and an amino acid sequence identical or homologous to p62; such proteins may be isolated from various species. By "homologous" it is intended that nucleotide sequences encoding homologous proteins are capable of hybridizing to the nucleotide sequence of encoding p62 under low stringency conditions, e.g., 40%–50% formamide, 37° C.–42° C., 4×SSC, and wash conditions (after several room temperature washes with 2×SSC, 0.5% SDS) of stringency equivalent to 37° C. with 1×SSC, 0.05% SDS. The "biological activity" of p62 is defined to include (1) the property of serving as a substrate for enzymes with tyrosine kinase activity, including such enzymes as v-arc, v-abl, and v-fps and (2) the property of binding to GAP. GAP derivatives, or molecules with GAP activity, e.g., when at least partially tyrosine phosphorylated. Furthermore, unless indicated otherwise, "p62" intends both phosphorylated and non-phosphorylated p62. By "phosphorylated", it is intended tyrosine phosphorylated, such that the phosphate groups are attached to one or more tyrosine residues.

By use of the term "GAP", it is intended not only the GAP protein, but derivatives of GAP capable of specifically binding to p62. Specifically included is the derivative of GAP referred to as GAP17, a derivative of GAP containing an epitope from SV40 Large T antigen (and thus immunoprecipitable by antibodies specific for the T antigen), Martin, et al., Cell, 63:843–849 (1990).

On the basis of DNA sequencing of several cDNA clones, human p62 has been determined to have an amino acid comprising the sequence of Table 1 [SEQ ID NO:1]. Table 1 represents a substantial portion of the amino acid sequence of human p62, but may lack some of the amino terminus amino acid sequence. The carboxy terminus of p62 is a tyrosine, which at the DNA level is followed by a UAA termination codon. The polypeptide represented by the amino acid sequence [SEQ ID NO:1] of Table 1 has 396 amino acids.

It will be appreciated that p62 from species other than humans may have amino acids sequences that differ from the human p62 sequence, but still possess p62 biological activity. For example, on the basis of nucleotide sequencing of the human p62 gene and the amino acid sequencing of mouse p62, the amino acid sequence of mouse p62 is known to differ from human p62 at least amino acid #112, as numbered in table 1, (an Arg to Met replacement) but still possess p62 biological activity.

The term p62 derivative is defined to include polypeptides possessing p62 biological activity and/or p62 immunological activity. By p62 immunological activity, it is intended that a polypeptide with p62 immunological activity can specifically bind with antibodies specific for p62, or can, upon injection with suitable adjuvants, be used to induce an immune response specific for p62. Unless indicated otherwise, the term "p62 derivative" means p62 derivatives with biological activity and p62 immunological activity.

Derivatives of p62 with p62 biological activity typically have amino acid sequences that consist of the amino acid sequence of p62 or the amino acid sequence [SEQ ID NO:1] of Table 1 with various minor variations. Derivatives of p62 may include polypeptides with the amino acid sequence of p62 with one or more amino acid substitutions. Preferably, these amino acid substitutions are the result of the substitution of one amino acid with another amino acid with a similar structure such as the replacement of a leucine with an isoleucine or valine, an aspartate with a glutamate, or a threonine with a serine, i.e., conservative amino acid replacements. Furthermore, p62 derivatives may include polypeptides with the amino acid sequence of p62 but possessing various minor amino acid deletions and/or insertions, typically in the range of about 1 to 5 amino acids, as well as one or more amino acid substitutions.

Other p62 derivatives may contain stretches of amino acid sequences that lack significant homology to p62 but possess one or more biological activity of interest. Such biological activities include enzymatic activity, such as β-galactosidase activity, and the ability to bind to specific, typically monoclonal, antibodies. These sequences lacking p62 homology are preferably located at the amino or the carboxy terminus portion of the p62 homologous region of the p62 derivative; however, enzymatically active amino acid sequences not homologous to p62 may be incorporated into the central region of the p62 homologous region of the p62 derivative. Furthermore, the term p62 derivative includes the polypeptide with the amino acid sequence [SEQ ID NO:1] of Table 1.

p62 and p62 derivatives may be derivatized by covalently attached modifying molecules that are not part of the polypeptide backbone of p62 or p62 derivatives. The modifying molecules may be attached by both biological, i.e., enzymatic, and synthetic means. Modifying molecules may include carbohydrates, lipids, water soluble polymers, or the like. P62 derivatives may possess glycosylation patterns that vary in accordance with the type of cell in which they are produced.

When modifying the amino acid sequence of p62 so as to give rise to biologically active p62 derivatives, it is important not to eliminate all of the tyrosine residues that are phosphorylated by tyrosine kinases. Tyrosine kinase consensus recognition sites has been identified, for example, see, Kemp and Pearson, TIBS, 15:342–346 (1990). As can be seen in Table 2, tyrosines that serve as substrates for tyrosine kinase activity are generally located near or bordering on acidic amino acid residues such as aspartic acid (D) or glutamic acid (E). Inspection of the amino acid of the sequence of p62 as represented in Table 1 reveals at least two potential tyrosine kinase receptor sites. Tyrosine #56 (as numbered in Table 1) and tyrosine #98 (as numbered in Table 1) appear to be substrates for tyrosine kinase activity. Moreover, phosphorylated p62 may be subjected to proteolytic digestion and the individual protease digestion fragments hydrolyzed and analyzed for the presence of phosphotyrosine so as to positively identify which tyrosine residues within p62 are phosphorylated by tyrosine kinases.

Similarly it is of interest to determine which residues or domains of p62 are required for GAP binding. Such GAP binding experiments may be performed, for example, by preparing various p62 derivatives (or fragments) and determining which of the p62 derivatives are capable of being immunoprecipitated by GAP-17 and antibodies specific for SV40 large T antigen domain of GAP-17. Other methods of identifying p62 domains required for GAP binding include performing western blots on partially protease digested p62 and developing the western blot with GAP (of a GAP derivative).

Homology searches of the NBRF amino acid sequence database using the amino acid sequence of Table 1, revealed significant homology between p62, and glycine-rich protein GRP33 from Artemia salina (brine shrimp). The FASTA program in the genetics computing group (Madison, Wis.) Comparison of the known p62 coding sequence of FIGS. 1a to 1d with the coding sequence the A. salinia glycine rich protein using the FASTA program, reveals an optimized matching score of 451, showing 57.3% identity in an overlap region of 588 base pairs. FIGS. 3 and 2 display comparisons of the homologus amino acid and nucleotide sequences, respectively. The homologous regions between p62 and the A. salina protein may provide guidance in the design of biologically active p62 derivatives.

Nucleotide Sequence of p62

The subject invention provides for purified nucleotide sequences encoding p62 and p62 derivatives. The nucleotide sequence [SEQ ID NO:2] of FIGS. 1a to 1d represent the human nucleotide sequence encoding the polypeptide sequence [SEQ ID NO:1] of Table 1 and 3' adjacent nucelotides that may not encode p62 but are part of the p62 gene transcript in that the sequences are derived from p62 encoding cDNA. The nucleotide sequence [SEQ ID NO:2] of FIGS. 1a to 1d is a composite made from overlapping human cDNA clones encoding portions of the p62 gene.

In addition to providing for nucleotide sequences with the sequence [SEQ ID NO:2] of FIGS. 1a to 1d, the subject invention also provides for numerous nucleotide sequences bearing homology to the nucleotide sequence of FIGS. 1a to 1d. Sequences of interest bearing homology to the nucleotide sequence [SEQ ID NO:2] of FIGS. 1a to 1d include nucleotide sequences encoding p62 or p62 derivatives.

It will be appreciated by those skilled in the art that as a result of the degeneracy of the genetic code, a multitude of nucleotide sequences, some bearing minimal nucleotide sequence homology to the nucleotide sequence [SEQ ID NO:2] of FIGS. 1a to 1d may be produced. The invention has specifically contemplated each and every possible variation of peptide or nucleotide sequence that could be made by selecting combinations based on the possible amino acid and codon choices made in accordance with the standard triplet genetic code as applied to the sequence of FIGS. 1a to 1d [SEQ ID NO:2] and all such variations are to be considered as being specifically disclosed.

Although nucleotide sequences encoding p62 and p62 derivatives are preferably capable of hybridizing to the nucleotide sequence [SEQ ID NO:2] of FIGS. 1a to 1d under stringent conditions, it may be advantageous to produce nucleotide sequences encoding p62 or p62 derivatives, possessing a substantially different coding sequences. Codons can be selected for use in a particular expression host organism in accordance with the frequency with which a particular codon is utilized by the host, if desired, to increase the rate at which expression of the peptide occurs. Other reasons for substantially altering the nucleotide sequence encoding p62/p62 derivatives without altering the amino acid sequence include the production of RNA transcripts having more desirable properties, e.g., greater half-life, than transcripts produced from the sequence [SEQ ID NO:2] of FIGS. 1a to 1d and the like.

Nucleotide sequences encoding p62 and p62 derivatives may be joined to a variety of other nucleotide sequences of interest by means of well established recombinant DNA techniques (see, for example, Sambrook, et al., *Molecular Cloning: A Laboratory Manual*, 2nd Ed., Cold Spring Harbor (1989).

Nucleotide sequences of interest for joining include an assortment of vectors, e.g., plasmids, cosmids, λ phage derivatives, phasmids, and the like, that are in the public domain. Vectors of interest include expression vectors, replication vectors, probe generation vectors, sequencing vectors, and the like. In general vectors of interest, may contain an origin of replication functional in at least one organism, convenient restriction endonuclease digestion sites, and selectable markers for the host cell.

Expression vectors may be used to express quantities of p62 or p62 derivatives in variety of cell hosts. Detailed descriptions of many expression vectors and their use can be found, for example in Goeddel, *Methods in Enzymology*, Vol. 185 (1990) Academic Press. Expression vectors contain promoters functional in the host of interest. The promoter may be operably linked to the coding sequence of a gene of interest so as to produce a translatable mRNA transcript encoding p62 or a p62 derivative. Expression vectors will generally have convenient restriction sites located near the promoter sequence so as to provide for the insertion of coding nucelic acid sequences. The promoters in suitable expression vectors may be either constituitive or inducible. In addition to having promoter sequences, expression vectors may contain various enhancer sequences and the like, included for the purpose of maximizing expression of p62 or p62 derivatives.

Another aspect of the subject invention is to provide for nucleic acid hybridization probes. Such probes may be used to isolate p62 and/or p62 homologous genes from genomic or cDNA libraries prepared from a variety of cells, in particular mammalian cells. Furthermore, nucleic acid hybridization probes may be used to detect the transcription of p62 or p62 homologous genes from a variety of organisms by means of northern blots, in situ hybridizations, and the like. Suitable nucleic acid hybridization probes for the detection of p62 and p62 homologous sequences comprise at least 14, preferably 25, and more preferably at least 500 nucleic acid bases pair from the sequence of [SEQ ID NO:2] FIGS. 1a to 1d. Hybridization probes may be labeled by a variety of labels including radionuclides, such as $^{32}p$ or $^{35}S$, or enzymatic labels such as alkaline phosphatase coupled to the probe via avidin/biotin coupling systems or the like.

Probes for hybridization may be synthesized by both enzymatic, and in vitro techniques. Short hybridization probes are preferably synthesized by in vitro methodology such as the use of commercially available DNA synthesizers such as Applied Biosystems machine.

An additional use for nucleic acid hybridization probes involves their use as primers for the polymerase chain reaction. The polymerase chain reaction is described in detail in U.S. Pat. Nos. 4,965,188 and 4,683,202 and 4,800,195.

Also of interest is the use of nucleotide sequences of the subject invention for the production of anti-sense RNA capable of hybridizing to p62 transcripts. Antisense RNA of interest may vary in length from about 14 nucleotides, to the entire p62 gene, and may include various non-coding region such as introns, untranslated regions, and the like. Endogenously produced or exogeneously added p62 anti-sense RNA may be used to attenuate the expression of p62 protein in cells of interest.

Other means of producing p62 hybridization probes include the cloning of nucleic acid sequences encoding p62 and p62 derivatives into vectors for the production of RNA probes. Such vectors are known in the art and are commerically available, and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding p62 or p62 derivatives entirely by synthetic chemistry, after which the gene can be inserted into any of the many available DNA vectors using reagents, vectors and cells that are freely available and in the public domain at the time of the filing of this application. Synthetic chemistry may be used to reproduce the entire sequence indicated in FIGS. 1a to 1d [SEQ ID NO:2], any portion thereof, or to introduce in mutations into the sequence.

For example, nucleotide sequences of length greater than 10 base pairs may be produced by commercially available machines. Oligonucleotides produced by in vitro synthesis may be readily spliced together using generally known recombinant DNA techniques. Salts of any of the macromolecules described herein will naturally occur when such molecules are present in (or isolated from) aqueous solutions of various pHs. All salts of peptides and other macromolecules having the indicated biological activity are considered to be within the scope of the present invention. Examples include alkali, alkaline earth, and other metal salts of carboxylic acid residues, acid addition salts (e.g., HCl) of amino residues, and zwitterions formed by reactions between carboxylic acid and amino residues within the same molecule.

Purification of p62

Sources of p62 and p62 Derivatives p62 and p62 derivatives may be purified from a variety of cells. By "purified" it is meant, when referring to a peptide of nucleotide sequence, that the indicated molecule is present in the substantial absence of other biological macromolecular, e.g., polypeptides, polynucleic acids, and the like of the same type. The term "purified" as used herein preferably means at least 95% by weight, more preferably at least 99.8% by weight, of biological macromolecules of the same type present (but water, buffers, and other small molecules, especially molecules having a molecular weight of less than 1000 can be present). The term "pure" is used herein preferably has the same numerical limits as "purified" immediately above. The term "isolated" as used herein refers to a polypeptide, polynucleotide molecules separated not only from other peptides, DNAs, or RNAs, respectively, that are present in the natural source of the macromolecule but also from other macromolecules and preferably refers to a macromolecule found in the presence of (if anything) only a solvent, buffer, ion or other component normally present in a solution of the same. "Isolated" and "purified" do not encompass either natural materials in their native state or natural materials that have been separated into components (e.g., in an acylamide gel) but not obtained either as pure substances or as solutions.

Suitable cell sources for the production of purified p62/p62 derivatives include cells naturally producing p62, cells not naturally encoding an expressible p62 gene but genetically modified to do so, and cells naturally producing p62 but genetically modified so as to produce elevated levels of p62. Preferred cell sources for p62 and p62 derivatives produce p62/p62 derivatives molecules so that at least 5%, preferably at least 50% and more preferably at least 90% of the p62/p62 derivative molecules are phosphorylated. Purification methods for p62/p62 derivatives that depend on affinity reagents specific for phosphotyrosine, necessarily employ p62/p62 derivatives isolated from cells that phosphorylate p62/p62 derivatives or from p62/p62 derivatives that have been produced in cells that lack phosphotyrosine activity but have been phosphorylated in vitro with enzymes with tyrosine kinase activity.

It will be appreciated that an important advantage of the subject invention is to apply recombinant DNA techniques so as to provide for cellular lysates that contain p62 in significantly higher, at least 2-fold, preferably at least 10-fold, higher concentrations than found in naturally occurring cells or cell lines that have not been modified by exogenous p62 encoding nucleic acid sequences. Since p62 derivatives are not naturally produced, it is apparent that cells from which p62 derivatives can be isolated do not naturally encode p62 derivatives but are genetically modified to do so.

Cells from which p62 and p62 derivatives may be isolated from include both prokaryotic and eukaryotic cells. Preferred cellular sources for the isolation of p62 and p62 derivatives include mammalian cells possessing high levels of tyrosine kinase activity, of particular interest are transformed mammalian cells expressing oncogenes with tyrosine kinase activity, oncogenes of interest include v-scr, v-abl, v-fps, v-fms and bcr/abl. A particularly preferred source of p62 is SRD 3T3 cells (v-scr transformed NIH 3T3 cells) available from the laboratory of Steve Martin at the University of California, Berkeley. Other mammalian cell sources of interest for the purification of p62 and p62 derivatives include mammalian cells stimulated by growth factors that bind to growth factor receptors that have tyrosine kinase activity. Another preferred source for preparations from which to purify p62 derivatives is insect cells, preferably grown in tissue culture, and genetically modified by baculovirus expression vectors or the like to express p62/p62 derivatives and a tyrosine kinase, preferably an oncogene encoded tyrosine kinase. A particularly preferred source of p62 derivatives is the SF9 cell line from *Spodoppdera frugiperda* (fall army worm) modified so as express v-src from expression vector AcVSR, Zhang, et al., *Cell, Physiol. and Biochem.*, 1:24–30 (1991) and a p62 derivative from expression vector pACC13.

Purification of p62 and p62 Derivatives

Affinity purification of p62 and p62 derivatives may employ various immobilized reagents specific for p62 or p62 derivatives, i.e., affinity reagents. The affinity purification may be performed in batches or employ chromatography columns. The affinity reagents may be immobilized to a variety of inert matrices prepared in bead form. References on how to perform affinity chromatography are readily available to those skilled in the art, exemplary of such references is Deutscher, *Guide to Protein Purification: Methods in Enzymology*, Vol. 182, Academic Press (1990). Suitable immobilization matrices include cross-linked agarose beads, Sepharose, cross-linked polyacrylamide beads, Sephacryl, and the like. When the affinity reagents used are antibodies, a preferred immobilizing matrix is protein A sepharose. Affinity reagents of interest include antibodies and GAP. Preferred affinity reagents for purification of p62/p62 derivative are phosphotyrosine-specific monoclonal antibodies. A particularly preferred phosphotyrosine-specific monoclonal antibody is FB2 (available from Rusty Williams at the University of California, San Francisco). Elution of p62/p62 derivatives may be eluted from the immobilized p62 specific reagents by means of solutions containing molecules that disrupt the interactions between the p62 specific reagent and p62/p62 derivative; such molecules may be inorganic or organic salts, or may be molecules bearing structural similarity to the region of p62/p62 derivative bound to the p62-specific affinity reagent. When the p62 specific affinity reagent is an anti-phosphotyrosine antibody, a preferred method of eluting p62 is by means of a phenyl phosphate solution having a concentration of about 25 mM. It will be appreciated by those skilled in the art that phosphotyrosine-specific monoclonal antibodies may be used to purify phosphorylated p62/p62 derivatives, but not non-phosphorylated p62/p62 derivatives. Purification of non-phosphorylated p62/p62 derivatives may also be achieved through the use of p62 specific antibodies as affinity reagents.

When purifying p62/p62 derivatives by means of an affinity reagent specific for phosphotyrosine and/or phosphorylated p62/p62 derivatives, the percentage of protein molecules phosphorylated and the amount of phosphorylation per molecule should be maximized so as to increase the yield of the purification procedure. The composition of the buffer in which the p62/p62 derivative lysate is prepared may have an effect on the yield of phosphorylated p62/p62 derivative obtained from the lysate. The presence of chelators, especially cation chetators such as EDTA, and the like, may reduce the yield of phosphorylated p62/p62 derivatives from cell lysate. Preferred lysate buffers do not contain EDTA or similar cation chelators. An important aspect of the subject invention is the discovery that omission of EDTA from cell lysis buffers significantly increases the amount of phosphorylated p62/p62 derivatives obtained from cells. Additional means of increasing the extent to which p62/p62 derivatives are phosphorylated include extended incubation of the cell lystate, preferably in the presence of protease inhibitors, prior to performing the purification procedure.

In addition to production of purified p62/p62 derivatives by purification of p62/p62 derivative produced in cells, purified p62/p62 derivatives may be produced by organic chemical reactions performed in vitro. Automated equipment for the direct synthesis of polypeptides disclosed herein is commercially available. Such equipment provides convenient access to peptides of the invention, either by direct synthesis or by synthesis of a series of fragments that can be coupled using other known techniques. The use of such commercially available polypeptide synthesis machines and the like are a preferred method of synthesizing oligopeptide p62 derivatives having about 5-25 amino acids.

Other methods for synthesis of p62/p62 derivatives include the in vitro transcription of p62/p62 derivative encoding DNA sequences coupled with the in vitro translation of the RNA transcripts thus produced. In vitro transcription systems are well known in the art. In vitro tranp-scription systems typically involve the creation of nucleotide sequences in which the coding sequence of interest is located downstream from a strong promoter, such as promoters specific for SP-6 or T7 RNA polymerases, followed by the addition of an RNA polymerase specific for the promoter, and substrates required for the reaction. Similarly, in vitro translation systems are well known in the art and may be used to produce p62/p62 derivative polypeptides from a variety of transcripts produced by in vitro transcription systems.

Uses for Purified p62 and p62 Derivatives p62 specific antibodies

The subject invention also provides for antibodies capable of specifically binding p62 or p62 homologous proteins. By the term "antibodies," it is intended both polyclonal and monoclonal antibodies with natural immunoglobulin sequences, synthetic antibody derivatives, and the like; antibodies may be modified so as to be joined to any of a variety of labels, fluorescent, radioactive, enzymatic, biotin/ avidin or the like. Synthetic antibody derivatives include natural immunoglobulin sequences that have been mutated and selected for altered binding specificity, various immunoglobulin gene derived polypeptides, typicaly single chain, produced by genetically modified bacteria, antibodies modified so as containing modified constant regions and the like; a review of such synthetic antibody derivatives based on the principles of antibody formation is provided in Winter and Milstein, *Nature*, 349: 293-299 (1991).

Antibodies of interest may be produced by using p62, or derivatives or fragment or peptides thereof, for the induction of specific antibodies. By induction of antibodies it is intended not only the stimulation of an immune response by injection into animals, but analogous steps in the production of synthetic antibodies such as the screening of recombinant immunoglobulin libraries, Orlandi et al., *PNAS USA* 86: 3833-3837 (1989) or Huse et al., *Science* 256: 1275-1281 (1989), or the in vitro stimulation of lymphocyte populations of particular not necessarily interest is the development of antibody preparations, mnonoclonal antibodies, specific for single epitopes on p62, i.e., monospecific antibodies.

P62 derivatives for use in the induction of antibodies of interest do not need to have p62 biological activity; however, p62 derivatives for use in the induction of antibodies will necessarily have immunological activity. Polypeptides for use in the induction of p62-specific antibodies may have an amino acid sequence consisting of at least five amino acids preferably at least 10 amino acids, mimicking a portion of the amino acid sequence of p62 and may contain the entire amino acid sequence of sequence p62.

Short oligopeptides, i.e., containing about 20 amino acids or less, are of particular interest for both the induction and the screening of mono-specific antibodies specific for epitopes of interest. In general, oligopeptides for use in the induction of epitope specific monospecific antibodies will have an amino sequence corresponding to at least a portion of the epitope of interest.

Of particular interest is the production of mono-specific antibodies specific for various epitopes of p62, such that sets of monospecific antibodies are developed that are capable of simultaneously binding, i.e., non-overlapping, to different regions of a p62 molecule. Reasons for the development of sets of simultaneously binding mono-specific antibodies include the production of immunoassays for the detection, quantitation, and measurement of the degree of phosphorylation, of p62. It is also of interest to produce antibody preparations that are capable of specifically binding to either the phosphorylated form of p62 or the non-phosphorylated form of p62, but not both. Uses for such phosphorylation state detecting antibodies include the measurement of the degree of phosphorylation of p62 in a cell.

Current technology, e.g., Winter and Milstein, *Nature*, 349:293-299 (1991), provides for a number of highly specific binding reagents based on the principles of antibody formation.

In a preferred embodiment of the subject invention, p62 and p62 derivative specific binding reagents are produced by the injection of p62 and/or p62 derivatives with immunological activity into mammals for the production of antisera or the production of hybridoma fusion partners. P62 and/or p62 derivatives for the induction of antibody response are preferably injected into mammals in conjunction with the presence of various adjuvants such as Freund's complete adjuvant, and the like, in order to maximize the immune response to p62 and/or p62 derivatives. More detailed descriptions of the methodology for the production of antibodies can be found in generally available publications such as Harlow and Lane, *Antibodies; a Laboratory Manual*, Coldspring Harbor Laboratory, Coldspring Harbor Press (1988).

Assays

The subject invention provides methods and reagents for performing assays capable of measuring the amount of tyrosine kinase activity present in a cell and the fraction of p62 molecules that are phosphorylated.

P62 and p62 derivatives, may be used as substrates for the detection and quantification of tyrosine kinase activity from a variety of cellular sources. It is desirable to measure tyrosine kinase activity for several reasons. Of particular interest is the measurement of tyrosine kinase activity produced by tyrosine kinases encoded by oncogenes and proto-oncogenes. Thus assays for tyrosine kinase may be employed to determine whether a cell is cancerous or has cancer potential. Also of interest is the measurement of tyrosine kinase activity attributable to the stimulation membrane bound ligand receptors with tyrosine kinase activity, since the extent of phosphorylation of p62 may be used to measure the extent to which ligands are binding to receptors.

Tyrosine kinase assays of interest measure the rate of phosphorylation of p62/p62 derivatives by tyrosine kinases in a cell, rather than simply measuring the amount of phosphorylated p62 present in a cell. Thus tyrosine kinase assays of interest employ a method for distinguishing tyrosine phosphorylation events that take place during an assay from tyrosine phosphorylation events that occur before an assay. Tyrosine kinase assays may employ the step of adding a phosphate source, preferably ATP and the like, to an assay mixture containing suitable buffers and salts. Phosphate sources may be radioactively labeled on the terminal phosphorous atom, so as to provide for the detection of kinase activity.

Tyrosine kinase activity assays employing radioactive labels may or may not employ the step of addition of p62/p62 derivatives, because tyrosine kinase substrates initially present in the cell or p62/p62 derivatives added externally, and subsequently phosphorylated by the radioactive phosphate source may subsequently be isolated by addition of p62-specific antibodies, followed by the step of radiometric quantition. Generally it will be preferable to add p62, preferably produced by recombinant means, to the assay mixture. After the kinase reaction has been allowed to progress, the amount of radioactive label incorporated into p62 is measured by radiometric means. In order to measure the amount of labeling, the unincorporated label must be removed prior to radiometric measurement. This removal can be achieved through a variety of means including immunoprecipitation of p62 with anti-p62 antibodies.

An important advantage of the subject invention is that the polypeptides provided for permit the detection and quantification of tyrosine kinase activity without requiring the addition of radioactively labeled phosphates. The absence of a need for a radionuclide label improves the safety and lowers the cost of performing assays. Methods for measuring tyrosine kinase activity without the addition radioactively labeled phosphates include assays involving the use of (1) p62 derivatives that contain epitopes not present on p62, (2) antibodies specific for that epitope, and (3) antiphosphotyrosine antibodies or GAP. Such assays involve the addition of the p62 derivatives to the assay mixture, followed by the immunoprecipitation or immunobilization of the p62 derivative by means of the epitope specific antibody so as to separate the p62 derivative from other cellular proteins containing phosphorylated tyrosine (including endogenous p62); the amount of phosphorylated p62 derivative complexed with the epitope specific antibody may then be measured by binding with phosphotyrosine-specific antibodies or GAP. GAP for use in the detection of phosphorylated p62/p62 derivatives may include GAP derivatives that have GAP activity.

In addition to providing methods and reagents for use in the detection of tyrosine kinase activity present in a cell, the subject invention provides methods and reagents for determining what fraction of the p62 in a cell is phosphorylated as well as determining the absolute amount of phosphorylated p62 present in a cell. By cell it is intended not only individual cells, but multiple cells. Tyrosine phosphorylation of p62 may be detected by a variety of means. If the phosphate source in the assay contains a radioactive label, then tyrosine kinase activity may be detected by separating the labeled p62 from the unincorporated label and quantitating the amount of label incorporated into the p62 substrate. When non-radioactively labeled phosphate sources are used in assays, phosphorylated p62 may be detected by means of generally known immunoassays in which the immunospecific reagant employed is specific for phosphotyrosine.

The subject invention provides for methods and reagents for performing assays capable of determining what fraction of p62 in a cell is phosphorylated. Such assay may employ well known immunoassay technology such as ELISA, RIA, western blotting, and the like; immunoassay technology of interest can be found, for example, in Tijssen, *Practice and Theory of Enzyme Immunoassays*, Elsevier Science Publishers (1985); Hudson and Hay, *Practical Immunology*, 3rd ed., Blackwell Scientific Publishers (1989). The use of p62 specific antibodies (as well as p62 and p62 derivatives) as provided for by the subject invention may be used in connection with the previously described well-established immunoassay technology in order to provide for assays capable of detecting the extent of p62 phosphorylation in a cell. In general, such assays will employ two types of p62-specific antibodies (or similar binding reagent) in an immobilized phase (1) antibodies capable of binding p62 in both phosphorylated and non-phosphorylated form or antibodies capable of binding only the non-phosphorylated form of p62, and (2) antibodies capable of binding the phosphorylated p62, or GAP/GAP derivatives that have similar specificity for the phosphorylated form of p62. By employing two types of specific binding reagent, it is possible to determine the relative quantities of the phosphorylated and unphosphorylated forms of p62 present in a sample. The binding of p62 (phosphorylated and non-phosphorylated) to an immobilized antibody phase may be detected by the addition of a third antibody, preferably labeled, and having an affinity for exposed epitopes on the antibody bound p62. Comparison of binding of the labeled antibody to p62 bound to the 2 different types of immobilized antibody may be used to determine the fraction of phosphorylated p62 present among the total p62 present in the sample.

P62 specific antibodies may also find use in the labeling of cells for use in techniques such as FACS, in situ immunohistological staining, and the like. p62 specific antibodies for use in such techniques are labeled, either directly or indirectly. The labeling of cells with p62-specific antibodies, especially antibodies specific for phosphorylated p62, find numerous uses including the detection of cancerous cells, precancerous cells, and cells stimulated by various growth factors.

The subject invention also provides for methods of measuring the quantity of GAP present in a sample. It is well established that GAP and p62 bind to each other when p62 is phosphorylated; this binding property may be exploited in assays for the quantity of GAP present in a sample. In general, p62 may be used to assay for GAP by method essentially the same as standard immunoassays involving antibodies specific for GAP, with the difference that p62 is substituted for anti-GAP antibodies. Although Table 1 does not provide the complete amino acid sequence of p62, and FIGS. 1a to 1d do not provide the complete nucleotide sequence of p62, it is apparent that the information provided herein is sufficient to enable one skilled in the art to obtain the complete amino acid sequence of p62 and the complete 5 nucleotide sequence of p62 by means of routine experimentation. Nucleic acid hybridization probes based on the sequence information of FIGS. 1a to 1d, preferably containing at least 0.5 kb of the sequence of FIGS. 1a to 1d and no base pair mismatches, may be used to probe a human genomic or cDNA library. Library isolates may then be sequenced by standard nucleic acid sequencing techniques. The sequence information may then be combined with information in Table 1 FIGS. 1a to 1d so as to provide for the complete nucleotide and amino acid sequences of human p62. Similarly, the nucleic acid and amino acid sequences of non-human p62 may be obtained by the hydrization probe screening of genomic and cDNA libraries prepared from corresponding non-human nucleic acid preparations.

On May 16, 1991, Applicants have deposited with the American Type Culture Collection, Rockville, Md., U.S.A. (ATCC) the plasmid pAC23-3, described herein ATCC accession no. 68624, and plasmid PAC37-6, described herein, given ATCC accession no. 68623. These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from date of deposit. The organisms will be made available by ATCC under the terms of the Budapest Treaty, and subject to an agreement between Applicants and ATCC which assures unrestricted availability upon issuance of the pertinent U.S. patent. Availability of the deposited strains is not to be construed as a license to practice the invention in contravention of the rights granted under the authority of any government in accordance with its patent laws.

TABLE 1

[SEQ ID NO:1]

| | |
|---|---|
| GGGSRGGARASPATQPPPLL | 20 |
| PPSATGPDATVGGPAPTPLL | 40 |
| PPSATASVKMEPENKYLPEL | 60 |
| MAEKDSLDPSFTHAMQLLTA | 80 |
| EIEKIQKGDSKKDDEENYLD | 100 |
| LFSHKNMKLKERVLIPVKQY | 120 |
| PKFNFVGKILGPQGNTIKRL | 140 |
| QEETGAKISVLGKGSMRDKA | 160 |
| KEEELRKGGDPKYAHLNMDL | 180 |
| HVFIEVFGPPCEAYALMAHA | 200 |
| MEEVKKFLVPDMMDDICQEQ | 220 |
| FLELSYLNGVPEPSRGRGVP | 240 |
| VRGRGAAPPPPPVPRGRGVG | 260 |
| PPRGALVRGTPVRGATTRGA | 280 |
| TVTRGVPPPPTVRGAPAPRA | 300 |
| RTAGIQRIPLPPPPAPETYE | 320 |
| EYGYDDTYAEQSYEGYEGYY | 340 |
| SQSQGDSEYYDYGHGEVQDS | 360 |
| YEAYGQDDWNGTRPSLKAPP | 380 |
| ARPVKGAYREHPYGRY | 396 |

TABLE 2

| Tyrosine kinases | |
|---|---|
| p60$^{v\text{-}src}$ | RLIEDNEYTARQGAK |
| p56$^{lck}$ | RLIEDNEYTAREGAK |
| p40$^{thymus}$ | PEEDGERYDEDEE |
| p85$^{gag\text{-}fes}$ | REEADGVYAASGGLR |
| p90$^{gag\text{-}yes}$ | RKIEDNEYTAREGAK |
| p120$^{gag\text{-}abl}$ | EEKEYHAE |
| EGF receptor | TAENAEYLRVAP |
| Insulin receptor | TRDIYETDYYRK |
| p75$^{liver}$ | DRVYVHPF |
| Spleen tyrosine kinase | EDAEYAARRRG |

Y indicates a phosphorylated tyrosine

The invention having been described, the following examples are offered to illustrate the subject invention by way of illustration, not by way of limitation.

EXAMPLES

V-8 Protease Digestion of p62

SRD 3T3 cell lysate was affinity purified with (antibodies specific for phosphotyrosine) and the purified material was subjected to SDS-polyacrylamide gel electrophoresis. A 62 Kd Coomaasie blue stained band excised from the gel was subsequently treated with *S. aureus* V-8 protease in situ in a tricine-SDS acrylamide according to the procedure of Schugger and Von Jagow, *Anal. Biochem*, 166:368–379 (1987). The excised bands were equilibrated in 15 ml solution of 25 mM Tris, pH 6.5, 1 mM DTT, 0.1% SDS, 20% (w/v) glycerol for a period of 5–10 minutes. The gel slice was then inserted into the well of Tris-Trycine SDS 10% polyacrylamide gel. The bands placed in the wells were then overlayed with 25 ml of a solution of 25 mM Tris pH 6.5, 0.1% SDS, 1 mM DTT and 20% glycerol overlay was applied, a second over 25 ul overlay was added of a solution containing 25 mM Tris pH 6.5, 0.1% SDS, 1 mM DTT, 10% glycerol, and *S. Aureus* V-8 protease (25 mg/ml). The gel was subsequently run at 20 mAmp until the dye front reached the stacking gel: resolving gel interface. The power supply for the electrophoresis was turned off when the dye front reached the interface, and subsequently turned back on 30 minutes later.

After the gel run was completed, i.e., when the dye front reached the bottom, the gel was electroblotted to a PVDF membrane (prewetted in methanol) in 10 mM CAPS/10% Methanol transfer buffer, for 30 minutes at 300 mA. After the gel proteins have been transferred to the membrane, the membrane was strained in 0.1% Coomasie blue, 50% methanol for 4–5 minutes and destained with a solution of 50% methanol/10% Acetic acid, followed by a rinse in water. Three bands were excised from the membrane and subjected to $NH_2$-terminal amino acid sequence analysis.

The following amino acid sequences were obtained from the excised bands. The amino acid sequence in the parentheses was uncertain.

1) NKYLPELMAEKDDLLPG [SEQ ID NO: 3]

2) LSYLNGVPEPS(LGG) [SEQ ID NO: 4]

Chymotrypsin Digestion

Essentially the same procedure used to obtain protease digestion fragments of p62 with *S-aureus* v-8 was repeated with chymotrypsin.

A composite amino acid sequence derived from two partial digestion bands is as follows:

1) KLKEMVLIPVKQYPKF [SEQ ID NO: 5]

Purification of p62

SRD 3T3 cells (v-src transformed NIH 3T3 cells) were grown in 800 $cm^3$ roller bottles in DME media (with 10% Calf Serum and pen./strep.) under standard growth conditions until about $10^8$ $10^9$ cells were present in each bottle. About 20 bottles were used. After growth, the cells were washed with cold PBS (phosphate buffered saline formula). The bottles were subsequently centrifuged at 12,000 rpm for 20 minutes, at 4° C., in a JA-20 rotor (Sorval). The pellets were subsequently resuspended on ice and pooled into a single beaker. A similar preparation of SRD 3T3 cells grown in suspension cultures, in the same media was also prepared. 22 gms of cells were obtained from the suspension culture. The procedure listed below was performed with the cells grown in suspension culture. A similar procedure was performed for the cells grown in the roller bottles 150 ml of RIPA lysate buffer was subsequently added to the cells with stirring by a stir bar on ice for a period of five minutes.

| | |
|---|---|
| 4.5 ml | 5 M Nacl |
| 7.5 ml | 1 M Tris pH 8.0 |
| 112.9% ml $H_2O$ | |
| 150λ Leupeptin | 10 mg/ml |
| 150λ Pepstatin | 10 mg/ml |
| 150λ Sodium Orthovanadate | 200 mM |
| 750λ Aprotinin | 2 mg/ml |
| 750λ PMSF | 200 mg/ml |

After the cells had been resuspended in the RIPA lysate buffer the following detergent mixture was added. Cell solutions made up in $H_2O$ 7.5 ml 10% (w/v) deoxycholate 15 ml 10% (w/v) $NaPO_4$ 0.75 ml 20% (w/v) SDS After the detergent mixture had been added the mixture was allowed to incubate on ice for a period of five minutes. After the incubation, the mixture was subsequently centrifuged at 12,000 rpm for a period of 20 minutes at 4° C. The cleared lysate was saved and stored overnight at −70° C.

The cell lysate was allowed to thaw and subsequently subjected to an affinity purification by batch absorption. 1.5 ml of Py FB2 (an anti-phosphotyrosine monoclonal antibody) bound to protein A sepharose and cross-linked with dimethylpimelimidate was added to 160 ml of the cell lysate. The absorption was allowed to proceed for two hours at 4° C. with rocking. The beads were subsequently washed with phosphate buffered saline and 0.5% $NaPO_4$ and transferred to a column. The column was subsequently equilabrated with elution buffer (without phenyl phosphate).

| | |
|---|---|
| 30 mM | Tris pH 8.0 |
| 80 mM | NaCl |
| 2 mM | $MgCl_2$ |
| 1 mM | DTT |
| 0.1% | $NaPO_4$ |
| 25 mM | Phenyl phosphate |

The proteins were subsequently eluted from the column with elution buffer containing 25 mM phenyl phosphate. Fractions of 0.5 ml were collected. The first two fractions of the column were void volumes. A total of eight 0.5 ml fractions were collected from the column. Fractions 3–6 contained a protein with a relative molecular weight of about 62 kd as detected by SDS-PAGE stained with Coomasie blue. Fractions 5 and 6 primarily contained p62, whereas fractions 2–4 contained significant quantities of other proteins. The estimated yield of p62 was about 200 micrograms (per 20 grams of cell paste).

Fractions 3–5 were subsequently pooled and concentrated in a speed vac concentrator. The pooled fractions were then subjected to SDS-PAGE on a 6% gel. The gel was stained with Coomasie blue and the p62 band subsequently excised for injection into rabbits.

Isolation of p62 cDNA Clones

A first screening of a commercially available human placental cDNA λ gt11 library (obtained from Clonetech, library #HL10086) was performed using consensus sequence probe GW62 [SEQ ID NO:6]. Approximately $2.5 \times 10^5$ plaques were screened using standard nucleic acid hybridization protocols performed under non-stringent conditions. Duplicate plaque lifts were made. $^{32}$P-labeled probes were made by kinasing oligonucleotide GW62 [SEQ ID NO:6].

Hybridization was performed using a solution containing 5× SSC, 5× Denhardt's solution, 50 mM $NaPO_4$ pH 7.0, 0.1% SDS, 100 micrograms/ml carrier DNA, for use as a prehybridization solution. Prehybridization took place for one hour and hybridization was allowed to proceed overnight at 37° C. The filters were initially washed with a solution containing 5× SSC and 0.5% SDS at room temperature. Subsequent washes at room temperature used 2× SSC and 0.1% SDS and were repeated until background radiation appeared to be minimized. 20 hybridization positive plaques were found. The 20 positive clones were subsequently screened for hybridization with consensus sequence probe GW68 [SEQ ID NO:7]. One positive clone was found upon rescreening with GW68 [SEQ ID NO:7]. The insert from the clone was subsequently excised by restriction digestion with EcoR I and cloned into the EcoR I site of commercially available plasmid pGEM (Promega Biotech). The pGEM vector containing the insert, a 1.4 kb insert, was subsequently called pG11.

A second screening of the same human placental λ gt11 library was performed under more stringent conditions. A new plating of the same library was screened. This second screening was performed essentially as the first library screening with the exception that the hybridization took place at 41° C., and the filter probe washings took place at 42° C. Furthermore, duplicate filters were independently probed with GW62 [SEQ ID NO:6] and GW68 [SEQ ID NO:7]. The second screening resulted in the detection of 8 plaques that hybridized with both probes. The longest clone forming the plaque was subsequently digested with EcoR I and a 2.3 kb insert was isolated and recloned into pGEM. The resultant plasmid was called pG23-3.

A third screening was performed using the same human placental λ GT11 library. A new plating of the library containing $4 \times 10^5$ plaques was screened. Screening was performed using an exact match probe GW74 [SEQ ID NO:8]. Screening was performed under stringent conditions. The hybridization protocol was essentially as used for the other screenings with the exception that the hybridization solution contained 40% (w/v) formamide, and was performed at 42° C. The filters were washed in 0.2× SSC and 0.1% SDS at 42° C. The hybridization resulted in detection of 30 plaques. Plaque number 37 was found to contain a 1.4 kb insert extending approximately 100 bp more 5' that the 5' end of the p611 insert found in the first screening of the library. The insert was subsequently excised an inserted into pACC13 so as to produce plasmid pAC37-6.

Expression of p62 in Baculovirus Vectors

The 2.3 kb p62 insert from pG23 was excised by EcoR I digestion and subsequently ligated into the EcoR I site of baculovirus expression vector pAcC13 using standard recombinant DNA techniques so as to give rise to plasmid pAC23-3. Similarly the insert from the λgt11 was inserted into the EcoR I site of pAcC13 to give rise to pAC37-6. Details on the use of baculovirus expression systems can be found, e.g., in Smith, et al., *Mol. Cell Biol.*, 3:2156–2165 (1983), Summers, et al., *Texas Agricultural Experiment Station Bulletin*, 155 (1987), and Luckow and Summers, *Bio/Technology*, 6:47–55 (1988). Plasmid pAC23-3 and pAC23-1 a plasmid essentially the same as pAC23-3 but containing the 2.3 kb insert in the reverse orientation, were transfected into Sf 9 cells. The baculovirus expression v-src, vectors containing the 2.3 kb insert were co-transfected with virus Acvsre a baculovirus capable of expressing vsrc, an oncogene encoded tyrosine kinase having tyrosine kinase activity on p62. Control cell lines were also set up containing only pAC23-3 and pAcC13, as well as the v-src expression vector alone. The transfected cell cultures were subsequently lysed, and the lysates were separated by SDS-PAGE and subsequently blotted onto nitrocellulose filters using standard western blotting techniques. The blots were subsequently probed with a GAP-17, a derivative of GAP having a specificity for phosphorylated p62 but containing an SV40 large T antigen epitope. The blots exposed to the GAP-17 were sequently probed with enzymatically labeled antibody KT3, a monoclonal specific for the large T antigen. Analysis of the blots revealed that GAP-17 bound specifically to a 52 kd bank present in insect cells containing both the v-src expression vector and pAC23-3. The predicted molecular weight of the portion of p62 encoded by the 2.3 kb insert placed into a pAC23-3 is approximately 52 kd. Thus, these results indicate that the portion of p62 expressed from pAC23-3 is functionally expressed in hornworm cells and is fully capable of being tyrosine phosphorylated and retaining its biological activity with respect to GAP binding.

Nucleic Acid Hybridization Probes

Nucleic acid hybridization probes were synthesized in vitro in accordance with amino acid sequences obtained from sequencing the $NH_2$-termini of p62 chymotrypsin and V-8 protease digestion fragments. Oligonucleotide probe GW62 [SEQ ID NO:6] was produced based on V-8 digest amino acid sequence 1 [SEQ ID NO: 3]. Oligonucleotide probe GW68 [SEQ ID NO:7] was produced based on chymotrypsin digest amino acid sequence 1 [SEQ ID NO:3].

Oligonucleotide probes GW74 [SEQ ID NO:8], GW78 [SEQ ID NO:9], GW79 [SEQ ID NO:10], are based on exact matches to regions of the p62 cDNA sequence in Table 2 [SEQ ID NO:2].

GW62: 5' AACAAGTACCTGCCTGAGCTGATGGCT-GAGAA 3' [SEQ ID NO:6]

GW68: 5' AAGGAGATGGTGCTGATCCCTGTGAAG-CAGTA 3+ [SEQ ID NO:7]

GW74: 5' AACAAGTACCTGCCCGAACTCATGGC-CGAGAAG 3' [SEQ ID NO:8]

GW78: 5' AGATGGAGCCAGAGAACAA 3' [SEQ ID NO:9]

GW79: 5' CCTGCAGTCTTTTGATTGTA 3' [SEQ ID NO:10]

Northern Blot Analysis

PolyA RNA preparations were prepared from MCF-7 cells (a human breast carcinoma cell line), MRC5 cells (a human lung fibroblast cell line), and human placental tissue cells. PolyA RNA was prepared by standard procedures. Approximately 4 micrograms of RNA was added to each well of a gel for electrophoretic separation. The separated RNA was then blotted onto nitrocellulose membrane by the standard northern blot procedure. The membrane was subsequently probed with probes made by PCR amplifying plasmid pAC37 with primers GW78 [SEQ ID NO: 9] and GW79 [SEQ ID NO:10]. Probes synthesized with $\alpha$ $^{32}$PdCTP and $\alpha$ $^{32}$PdGTP. The blot was hybridized overnight at 42° C. in a 50% formamide hybridization solution. The membrane was subsequently washed once in 2×SSC/0.1% SDS at 42° C. and 3 times in 0.2×SSC/0.19 SDS at 42° C. Exposure of the probe membrane to x-ray film overnight revealed the development of hybridization bands of approximately identical molecular weight of about 2.7 kb in the all of other RNA preparations. The results indicate that sequences encoding p62 are being transcribed in untransformed are well as transformed cells.

Determination of GAP Binding Domain of p62

Purified p62 was separately digested with S. aureus V-8 protease and chymotrypsin and the digestion fragments were subsequently separated from one another by PAGE and electrically transferred in situ to an immobilizing membrane, essentially as described above.

The blot was subsequently probed with GAP32, a GAP derivative containing only the SH2 domain. The GAP32 probe bound to 1 of the 3 major V-8 digestion bands and 3 of the 7–8 major chymotrypsin digestion bands.

The foregoing written specification is considered to be sufficient to enable one skilled in the art to practice the invention. Indeed, various modifications of the above-described modes for carrying out the invention which are obvious to those skilled in the field of pharmaceutical formulation or related fields are intended to be within the scope of the following claims.

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 396 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: C-terminal ( v i ) ORIGINAL SOURCE:
        ( A ) ORGANISM: Homo sapiens ( x i ) SEQUENCE DESCRIPTION: SEQ ID NO:1:

```
Gly Gly Gly Ser Arg Gly Gly Ala Arg Ala Ser Pro Ala Thr Gln Pro
 1               5                  10                  15

Pro Pro Leu Leu Pro Pro Ser Ala Thr Gly Pro Asp Ala Thr Val Gly
                20                  25                  30

Gly Pro Ala Pro Thr Pro Leu Leu Pro Pro Ser Ala Thr Ala Ser Val
                35                  40                  45

Lys Met Glu Pro Glu Asn Lys Tyr Leu Pro Glu Leu Met Ala Glu Lys
        50                  55                  60

Asp Ser Leu Asp Pro Ser Phe Thr His Ala Met Gln Leu Leu Thr Ala
```

-continued

```
            65                      70                      75                      80
    Glu  Ile  Glu  Lys  Ile  Gln  Lys  Gly  Asp  Ser  Lys  Lys  Asp  Asp  Glu  Glu
                        85                      90                      95

Asn  Tyr  Leu  Asp  Leu  Phe  Ser  His  Lys  Asn  Met  Lys  Glu  Lys  Glu  Arg
                        100                     105                     110

Val  Leu  Ile  Pro  Val  Lys  Gln  Tyr  Pro  Lys  Phe  Asn  Phe  Val  Gly  Lys
                        115                     120                     125

Ile  Leu  Gly  Pro  Gln  Gly  Asn  Thr  Ile  Lys  Arg  Leu  Gln  Glu  Glu  Thr
              130                     135                     140

Gly  Ala  Lys  Ile  Ser  Val  Leu  Gly  Lys  Gly  Ser  Met  Arg  Asp  Lys  Ala
    145                     150                     155                     160

Lys  Glu  Glu  Glu  Leu  Arg  Lys  Gly  Gly  Asp  Pro  Lys  Tyr  Ala  His  Leu
                        165                     170                     175

Asn  Met  Asp  Leu  His  Val  Phe  Ile  Glu  Val  Phe  Gly  Pro  Pro  Cys  Glu
                        180                     185                     190

Ala  Tyr  Ala  Leu  Met  Ala  His  Ala  Met  Glu  Glu  Val  Lys  Lys  Phe  Leu
                        195                     200                     205

Val  Pro  Asp  Met  Met  Asp  Asp  Ile  Cys  Gln  Glu  Gln  Phe  Leu  Glu  Leu
              210                     215                     220

Ser  Tyr  Leu  Asn  Gly  Val  Pro  Glu  Pro  Ser  Arg  Gly  Arg  Gly  Val  Pro
    225                     230                     235                     240

Val  Arg  Gly  Arg  Gly  Ala  Ala  Pro  Pro  Pro  Pro  Val  Pro  Arg  Gly
                        245                     250                     255

Arg  Gly  Val  Gly  Pro  Pro  Arg  Gly  Ala  Leu  Val  Arg  Gly  Thr  Pro  Val
                        260                     265                     270

Arg  Gly  Ala  Ile  Thr  Arg  Gly  Ala  Thr  Val  Thr  Arg  Gly  Val  Pro  Pro
                        275                     280                     285

Pro  Pro  Thr  Val  Arg  Gly  Ala  Pro  Ala  Pro  Arg  Ala  Arg  Thr  Ala  Gly
              290                     295                     300

Ile  Gln  Arg  Ile  Pro  Leu  Pro  Pro  Pro  Pro  Ala  Pro  Glu  Thr  Tyr  Glu
    305                     310                     315                     320

Glu  Tyr  Gly  Tyr  Asp  Asp  Thr  Tyr  Ala  Glu  Gln  Ser  Tyr  Glu  Gly  Tyr
                        325                     330                     335

Glu  Gly  Tyr  Tyr  Ser  Gln  Ser  Gln  Gly  Asp  Ser  Glu  Tyr  Tyr  Asp  Tyr
                        340                     345                     350

Gly  His  Gly  Glu  Val  Gln  Asp  Ser  Tyr  Glu  Ala  Tyr  Gly  Gln  Asp  Asp
                        355                     360                     365

Trp  Asn  Gly  Thr  Arg  Pro  Ser  Leu  Lys  Ala  Pro  Pro  Ala  Arg  Pro  Val
              370                     375                     380

Lys  Gly  Ala  Tyr  Arg  Glu  His  Pro  Tyr  Gly  Arg  Tyr
    385                     390                     395
```

( 2 ) INFORMATION FOR SEQ ID NO:2:

( i ) SEQUENCE CHARACTERISTICS:
        ( A ) LENGTH: 1485 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( v i ) ANTI-SENSE: N ( v i ) ORIGINAL SOURCE:
        ( A ) ORGANISM: Homo sapiens ( x i ) SEQUENCE DESCRIPTION: SEQ ID NO:2:

```
CGGGGGGGGA TCCCGCGGGG GCGCCCGGGC CTCGCCCGCC ACGCAGCCGC CACCGCTGCT     60
GCCGCCCTCG GCCACGGGTC CCGACGCGAC AGTGGGCGGG CCAGCGCCGA CCCCGCTGCT    120
GCCCCCCTCG GCCACAGCCT CGGTCAAGAT GGAGCCAGAG AACAAGTACC TGCCCGAACT    180
CATGGCCGAG AAGGACTCGC TCGACCCGTC CTTCACTCAC GCCATGCAGC TGCTGACGGC    240
AGAAATTGAG AAGATTCAGA AAGGAGACTC AAAAAAGGAT GATGAGGAGA ATTACTTGGA    300
TTTATTTTCT CATAAGAACA TGAAACTGAA AGAGCGAGTG CTGATACCTG TCAAGCAGTA    360
TCCCAAGTTC AATTTTGTGG GGAAGATTCT TGGACCACAA GGGAATACAA TCAAAAGACT    420
GCAGGAAGAG ACTGGTGCAA AGATCTCTGT ATTGGGAAAG GGCTCAATGA GAGACAAAGC    480
CAAGGAGGAA GAGCTGCGCA AAGGTGGAGA CCCCAAATAT GCCCACTTGA ATATGGATCT    540
GCATGTCTTC ATTGAAGTCT TTGGACCCCC ATGTGAGGCT TATGCTCTTA TGGCCCATGC    600
CATGGAGGAA GTCAAGAAAT TTCTAGTACC GGATATGATG GATGATATCT GTCAGGAGCA    660
ATTTCTAGAG CTGTCCTACT TGAATGGAGT ACCTGAACCC TCTCGTGGAC GTGGGGTGCC    720
AGTGAGAGGC CGGGGAGCTG CACCTCCTCC ACCACCTGTT CCCAGGGGCC GTGGTGTTGG    780
ACCACCTCGG GGGGCTTTGG TACGTGGTAC ACCAGTAAGG GGAGCCATCA CCAGAGGTGC    840
CACTGTGACT CGAGGCGTGC CACCCCCACC TACTGTGAGG GGTGCTCCAG CACCAAGAGC    900
ACGGACAGCG GGCATCCAGA GGATACCTTT GCCTCCACCT CCTGCACCAG AAACATATGA    960
AGAATATGGA TATGATGATA CATACGCAGA ACAAAGTTAC GAAGGCTACG AAGGCTATTA   1020
CAGCCAGAGT CAAGGGGACT CAGAATATTA TGACTATGGA CATGGGGAGG TTCAAGATTC   1080
TTATGAAGCT TATGGCCAGG ACGACTGGAA TGGGACCAGG CCGTCGCTGA AGGCCCCTCC   1140
TGCTAGGCCA GTGAAGGGAG CATACAGAGA GCACCCATAT GGACGTTATT AAAAACAAAC   1200
ATGAGGGGAA AATATCAGTT ATGAGCAAAG TTGTTACTGA TTTCTTGTAT CTCCCAGGAT   1260
TCCTGTTGCT TTACCCACAA CAGACAAGTA ATTGTCTAAG TGTTTTCTT CGTGGTCCCC    1320
TTCTTCTCCC CACCTTATTC CATTCTTAAC TCTGCATTCT GGCTTCTGTA TGTAGTATTT   1380
TAAAATGAGT TAAAATAGAT TTAGGAATAT TGAATTAATT TTTAAGTGT GTAGATGCTT    1440
TTTTCTTTGT TGTTTAAATA TAAACAGAAG TGTACCTTTT ATAAT                    1485
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: N ( v ) FRAGMENT TYPE: internal ( v i ) ORIGINAL SOURCE:
        ( A ) ORGANISM: Mus musculus ( x i ) SEQUENCE DESCRIPTION: SEQ ID NO:3:

```
Asn Lys Tyr Leu Pro Glu Leu Met Ala Glu Lys Asp Asp Leu Leu Pro
 1               5                  10                  15
Gly
```

( 2 ) INFORMATION FOR SEQ ID NO:4:

( i ) SEQUENCE CHARACTERISTICS:
    ( A ) LENGTH: 14 amino acids
    ( B ) TYPE: amino acid
    ( D ) TOPOLOGY: linear ( i i ) MOLECULE TYPE: peptide ( i i i ) HYPOTHETICAL: N ( v i ) ANTI-SENSE: N ( v ) FRAGMENT TYPE: internal ( v i ) ORIGINAL SOURCE:
    ( A ) ORGANISM: Mus musculus ( x i ) SEQUENCE DESCRIPTION: SEQ ID NO:4:

Leu Ser Tyr Leu Asn Gly Val Pro Glu Pro Ser Leu Gly Gly
1               5                   10

( 2 ) INFORMATION FOR SEQ ID NO:5:

( i ) SEQUENCE CHARACTERISTICS:
    ( A ) LENGTH: 16 amino acids
    ( B ) TYPE: amino acid
    ( D ) TOPOLOGY: linear ( i i ) MOLECULE TYPE: peptide ( i i i ) HYPOTHETICAL: N ( v ) FRAGMENT TYPE: internal ( v i ) ORIGINAL SOURCE:
    ( A ) ORGANISM: Mus musculus ( x i ) SEQUENCE DESCRIPTION: SEQ ID NO:5:

Lys Leu Lys Glu Met Val Leu Ile Pro Val Lys Gln Tyr Pro Lys Phe
1               5                   10                  15

( 2 ) INFORMATION FOR SEQ ID NO:6:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: Y ( i v ) ANTI-SENSE: N ( v i ) ORIGINAL SOURCE:
    ( A ) ORGANISM: Mus musculus ( x i ) SEQUENCE DESCRIPTION: SEQ ID NO:6:

AACAAGTACC TGCCTGAGCT GATGGCTGAG AA                                 32

( 2 ) INFORMATION FOR SEQ ID NO:7:

( i ) SEQUENCE CHARACTERISTICS:
    ( A ) LENGTH: 32 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: Y ( v i ) ANTI-SENSE: N ( v i ) ORIGINAL SOURCE:
        ( A ) ORGANISM: Mus musculus ( x i ) SEQUENCE DESCRIPTION: SEQ ID NO:7:

AAGGAGATGG TGCTGATCCC TGTGAAGCAG TA    32

( 2 ) INFORMATION FOR SEQ ID NO:8:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: NA ( i i i ) HYPOTHETICAL: N ( v i ) ANTI-SENSE: N ( v i ) ORIGINAL SOURCE:
        ( A ) ORGANISM: Homo sapiens ( x i ) SEQUENCE DESCRIPTION: SEQ ID NO:8:

AACAAGTACC TGCCCGAACT CATGGCCGAG AAG    33

( 2 ) INFORMATION FOR SEQ ID NO:9:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( v i ) ANTI-SENSE: N ( v i ) ORIGINAL SOURCE:
        ( A ) ORGANISM: Homo sapiens ( x i ) SEQUENCE DESCRIPTION: SEQ ID NO:9:

AGATGGAGCC AGAGAACAA    19

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: N ( v i ) ANTI-SENSE: N ( v i ) ORIGINAL SOURCE:
        ( A ) ORGANISM: Homo sapiens ( x i ) SEQUENCE DESCRIPTION: SEQ ID NO:10:

CCTGCAGTCT TTTGATTGTA    20

We claim:

1. A purified and isolated polynucleotide comprising a contiguous subsequence of at least 14 nucleotides of SEQ ID NO: 2.

2. A purified and isolated polynucleotide comprising a nucleotide sequence encoding the amino acid sequence of SEQ ID NO:1.

3. A purified and isolated polynucleotide according to claim 2, wherein said polypeptide is able to specifically interact with GAP.

4. An expression vector, said vector comprising a promoter operably linked to a nucleotide sequence according to claim 2.

5. An expression host cell, said cell comprising a vector according to claim 4.

6. A nucleic acid hybridization probe, said probe comprising a polynucleotide according to claim 1, and a detectable label joined to said polynucleotide.

7. The purified and isolated polynucleotide of claim 1, comprising a contiguous subsequence of at least 25 nucleotides of SEQ ID NO: 2.

8. The purified and isolated polynucleotide of claim 1, comprising a contiguous subsequence of nineteen nucleotides of SEQ ID NO: 2.

9. The purified and isolated polynucleotide of claim 8, comprising SEQ ID NO: 9.

10. The purified and isolated polynucleotide of claim 1, comprising a contiguous subsequence of 20 nucleotides of SEQ ID NO: 2.

11. The purified and isolated polynucleotide of claim 10, comprising SEQ ID NO: 10.

12. The purified and isolated polynucleotide of claim 7; wherein said polynucleotide has a nucleotide sequence selected from the group consisting of SEQ ID NO: 6, SEQ ID NO: 7 and SEQ ID NO: 8.

13. The nucleic acid hybridization probe of claim 6, wherein said probe comprises a contiguous subsequence of at least 25 nucleotides of SEQ ID NO: 2.

14. The nucleic acid hybridization probe of claim 6, wherein said probe comprises a polynucleotide having a nucleotide sequence selected from the group consisting of SEQ ID NO: 6, SEQ ID NO: 7, SEQ ID NO: 8, SEQ ID NO: 9 and SEQ ID NO: 10.

* * * * *